(12) United States Patent
Rajeswaran

(10) Patent No.: US 12,714,576 B2
(45) **Date of Patent: *Aug. 25, 2026**

(54) SYSTEM AND METHOD FOR TREATMENT OF BONE

(71) Applicant: SHANKAR RAJESWARAN M.D. LLC, Chicago, IL (US)

(72) Inventor: Shankar Rajeswaran, Chicago, IL (US)

(73) Assignee: SHANKAR RAJESWARAN M.D. LLC

( * ) Notice: Subject to any disclaimer, the term of this patent is extended or adjusted under 35 U.S.C. 154(b) by 0 days.

This patent is subject to a terminal disclaimer.

(21) Appl. No.: 18/774,086

(22) Filed: Jul. 16, 2024

(65) Prior Publication Data

US 2024/0398581 A1 Dec. 5, 2024

Related U.S. Application Data

(63) Continuation of application No. 17/379,926, filed on Jul. 19, 2021, now Pat. No. 12,090,065.

(Continued)

(51) Int. Cl.
*A61F 2/46* (2006.01)
*A61B 17/34* (2006.01)

(Continued)

(52) U.S. Cl.
CPC ........ *A61F 2/4601* (2013.01); *A61B 17/3403* (2013.01); *A61B 17/3472* (2013.01);

(Continued)

(58) Field of Classification Search
CPC ............ A61B 17/3472; A61B 17/8805; A61B 17/8827; A61B 17/8855; A61F 2/4601
See application file for complete search history.

(56) References Cited

U.S. PATENT DOCUMENTS 7,771,431 B2 * 8/2010 Scribner ............ A61B 17/8833 606/93
12,090,065 B2 * 9/2024 Rajeswaran ............ A61L 27/50

FOREIGN PATENT DOCUMENTS

EP 3 359 209 A1 8/2018

OTHER PUBLICATIONS

Pasetti and Gandolfo, "CIRSE 2017", Cardiovascular and Interventional Radiology, Springer Verlag, Inc., New York, US, vol. 40, No. Suppl 2, P-90, Aug. 1, 2017, pp. 25-412; DOI: 10.1007/S00270-017-1725-Y (Year: 2017).*

(Continued)

*Primary Examiner* — Larry E Waggle, Jr.
(74) *Attorney, Agent, or Firm* — SQUIRE PATTON BOGGS (US)

(57) ABSTRACT

The invention as described herein provides methods for treating a bone of a patient, including locating a treatment volume in a bone of the patient, administering a sclerosing agent to the treatment volume, and, after administering the sclerosing agent, administering bone graft material to the treatment volume. In some embodiments, the sclerosing agent and the bone graft are administered in a minimally invasive manner using a delivery device. The placement of the delivery device and/or the administration of the sclerosing agent and/or bone graft can use imaging to guide the placement and/or administration. The patient can be a pediatric patient and the treatment volume can comprise a bone lesion, a unicameral bone cyst or an aneurysmal bone cyst.

20 Claims, 8 Drawing Sheets

Related U.S. Application Data

(60) Provisional application No. 63/054,759, filed on Jul. 21, 2020.

(51) Int. Cl.
*A61B 17/88* (2006.01)
*A61K 9/00* (2006.01)
*A61K 31/65* (2006.01)

(52) U.S. Cl.
CPC ...... *A61B 17/8827* (2013.01); *A61B 17/8855* (2013.01); *A61K 9/0019* (2013.01); *A61K 31/65* (2013.01)

(56) References Cited

OTHER PUBLICATIONS

Interanational Search Report and Written Opinion of PCT/US2021/042241 dated Nov. 4, 2021; 15 pages.

BackTable Podcast: "Novel Treatment of Unicameral & Aneurysmal Bone Cysts w/ Dr. Shankar Rajeswaran j BT Podcast Ep. 131", Jun. 11, 2021, p. 1, XP054982387; Retrieved from the Internet: URL:https://www.youtube.com/watch?v=8GmtjVZd2M [retrieved on Oct. 25, 2021].

Batisse et al., "Aneurysmal bone cyst: A 19-case series managed by percutaneous sclerotherapy", Orthopaedics & Traumatology: Surgery & Research, vol. 102, No. 2, 2016, pp. 213-216; DOI: 10.1016/J.OTSR.2015.11.016.

Boseker et al., "A clinicopathologic study of simple unicameral bone cysts", Surgery, Gynecology & Obstetrics, Sep. 1968; 127:550-560. PMID: 4874360.

Campanacci et al., "Unicameral and aneurysmal bone cysts", Clinical Orthopaedics, 1986, 204:25-36.

Canavese et al., "Unicameral bone cysts: comparison of percutaneous curettage, steroid, and autologous bone marrow injections", J Pediatr Orthop., Jan./Feb. 2011, vol. 31, No. 1, pp. 50-55. doi: 10.1097/BPO.0b013e3181ff7510.

Capanna et al., "The natural history of uni-cameral bone cyst after steroid injection", Clinical Orthop and Related Research, Jun. 1982, vol. 166, pp. 204-211.

Cho HS, et al., "Unicameral bone cysts: A comparison of injection of steroid and grafting with autologous bone marrow", The journal of Bone and Joint Surgury, Feb. 2007, vol. 89-B, No. 2, pp. 222-226. DOI: 10.1302/0301-620X.89B2.18116.

Cohen J., "Etiology of simple bone cyst", J Bone Jt Surg Am., Oct. 1970, 52:1493-1497.

D'Amato et al., "Treatment of simple bone cyst with bone marrow concentrate and equine-derived demineralized bone matrix injection versus methylprednisolone acetate injections: A retrospective comparative study", Acta Orthop Traumatol Turc., 2020, vol. 54, No. 1, pp. 49-58. doi: 10.5152/j.aott.2020.01.371.

De Grauw et al., "Inflammatory mediators and cartilage biomarkers in synovial fluid after a single inflammatory insult: a longitudinal experimental study", Arthritis Research and Therapy, 2009, vol. 11, No. 2, pp. 1-8; doi:10.1186/ar2640.

De Maria et al., "Sclerotherapy for lymphatic malformations of head and neck: systematic review and meta-analysis", J Vasc Surg Venous Lymphat Disord. 2020; 8:154-164. doi: 10.1016/j.jvsv.2019.09.007.

Evaniew et al., "Use of a calcium sulfate-calcium phosphate synthetic bone graft composite in the surgical management of primary bone tumors", Orthopedics, Feb. 2013, vol. 36, No. 2, pp. e216-e222; doi: 10.3928/01477447-20130122-25.

Evans et al., Unicameral bone cyst. In: StatPearls [Internet]. Treasure Island (FL): StatPearls Publishing; Jan. 2021, pp. 1-4; Available from https://www.ncbi.nlm.nih.gov/books/NBK470587/?report=printable.

Fahey JJ, et al., "Subtotal resection and grafting in selected cases of solitary unicameral bone cyst", The Journal of Foot and Ankle Surgery, Jan. 1973, vol. 55-A, pp. 59-68.

Farr et al., "Current trends and variations in the treatment of unicameral bone cysts of the humerus: a survey of EPOS and POSNA members", J Pediatr Orthop., Jan. 2020, vol. 40, No. 1, pp. e68-e76. doi: 10.1097/BPO.0000000000001376.

Galasko CSB, "The fate of simple bone cysts which fracture", Letters to the Editor, Clinical Orthopaedics and Related Researche, Jun. 1974, No. 101, pp. 302-304.

Gartland et al., "Modern concepts in the treatment of unicameral bone cysts of the proximal humerus", Orthopedic Clinics of North America, Apr. 1975, vol. 6, No. 2, pp. 487-498.

Gentile JV, et al., "Treatment of unicameral bone cysts in pediatric patients with an injectable regenerable graft: a preliminary report", *J Pediatr Orthop*., Apr. 1, 2013; 33:254-261. doi: 10.1097/BPO.0b013e318285c56c.

Goel et al., "Unicameral bone cysts: Treatment with methylprednisone acetate injections", The Journal of Foot and Ankle Surgery, American College of Foot and Ankle Surgeons, Nov. 1, 1994, vol. 33, No. 1, pp. 6-15.

Hagmann et al., "Mid- and long-term clinical results of surgical therapy in unicameral bone cysts", BMC Musculoskeletal Disordorders, 2011, 12:281; doi: 10.1186/1471-2474-12-281; http://www.biomedcentral.com/1471-2474/12/281.

Hou et al., "Treatment of unicameral bone cyst: a comparative study of selected techniques", *J Bone Joint Surg Am*. 2010;92:855-62. doi: 10.2106/JBJS.I.00607.

Hou et al., "Treatment of unicameral bone cyst: Surgical Technique", Journal of Bone and Joint Surgery, vol. 93, No. Supplement_1, Mar. 16, 2011, pp. 92-99; Doi: 10.2106/JBJS.J.01123.

Kadhim et al., "Treatment of unicameral bone cyst: Systematic review and meta analysis", J Child Orthop. 2014, 8:171-191. doi: 10.1007/s11832-014-0566-3.

Kaelin A., Kyste essential des os. Cahiers d' enseignement de la SOF-COT. Paris: Expanzion Scientifique Francaise; 1995:167-179 with an English abstract/conclusion.

Karr, Jeffrey, "Calcium sulfate/calcium phosphate bone void filler in the treatment of bilateral adolescent unicameral calcaneal bone cysts: 36-month follow-up", Journal of the American Podiatric Medical Association, Sep./Oct. 2019, vol. 109, No. 5, pp. 379-388.

Landgraeber et al., "Modifications to advanced core decompression for treatment of avascular necrosis of the femoral head", BMC Musculoskeletal Disorders, 2017; 18:479. doi: 10.1186/s12891-017-1811-y.

Lopez JJ, et al., "Sclerotherapy for splenic cysts in children", J Surg Res., Nov. 2017; 219:1-4; doi: 10.1016/j.ss.2017.05.029.

Mascard et al., "Bone cysts: unicameral and aneurysmal bone cyst", Orthopaedics & Traumatology: Surgery & Research 101, 2015, pp. S119-S127; http://dx.doi.org/10.1016/j.otsr.2014.06.031.

Neer, Charles et al., "Current concepts on the treatment of solitary unicameral bone cyst", Clin Orthop, Nov.-Dec. 1973, No. 97, pp. 40-51.

Neer, II, et al., "Treatment of unicameral bone cyst: a follow-up study of one hundred seventy-five cases", *J Bone Joint Surg Am*., Jun. 1966, vol. 48-A, No. 4, pp. 731-745.

Noordin et al., "Unicameral bone cysts: Current concepts", Annals of Medicine and Surgery, 2018, vol. 34, pp. 43-49; https://doi.org/10.1016/j.amsu.2018.06.005.

Oppenheim et al., "Operative treatment versus steroid injection in the management of unicameral bone cysts", *J Pediatr Orthop*., 1984; 4:1-7. DOI: 10.1097/01241398-198401000-00001.

Pasetti and Gandolfo, "CIRSE 2017", Cardiovascular and Interventional Radiology, Springer Verlag, Inc., New York, US, vol. 40, No. Suppl 2, P-90, Aug. 1, 2017, pp. 25-412; DOI: 10.1007/S00270-017-1725-Y.

Pretell-Mazzini et al., "Unicameral bone cysts: general characteristics and management controversies", The American Academy of Orthopaedic Surgeons, May 2014, vol. 22, No. 5, pp. 295-303; doi: 10.5435/JAAOS-22-05-295.

PRO-DENSE® Injectable regenerative graft: In vitro and in vivo observations, and a proposed mechanism of action, Technical Monograph, Wright Medical Technology, Inc. 2014. Available from http://www.wrightemedia.com/ProductFiles/Files/PDFs/009555_EN_LR_LE.pdf.

(56) References Cited

OTHER PUBLICATIONS

Sakamoto et al., "Clinical outcome following surgical intervention for a solitary bone cyst: emphasis on treatment by curettage and steroid injection", Journal of Orthopaedic Science, Aug. 19, 2010; 15(4):553-559; DOI: 10.1007/s00776-010-1485-x.

Scaglietti et al., "The effects of methylprednisolone acetate in the treatment of bone cysts. Results of three years follow-up", The Journal of Bone and Joint Surgery, May 1979, vol. 61-B, No. 2, pp. 200-204.

Shiels II Do and Mayerson; "Percutaneous doxycycline treatment of aneurysmal bone cysts with low recurrence rate: a preliminary report", Clin Orthop Relat Res. 2013; 471:2675-2683. doi: 10.1007/s11999-013-3043-2.

Shindell R. et al., "Prostaglandin levels in unicameral bone cysts treated by intralesional steroid injection", J Pediatr Orthop., 1989; 9:516-519.

Sionek et al., "Hip osteonecrosis treated with calcium sulfate-calcium phosphate bone graft substitute have different results according to the causes of osteonecrosis: alcohol abuse or corticosteroid-induced", *International Orthopaedics*. 2018; 42:1491-1498. doi: 10.1007/s00264-018-3892-0.

Spence, Jr, et al., "Solitary unicameral bone cyst: treatment with freeze-dried crushed cortical bone allograft. A review of one hundred and forty-four cases", The Journal of Bone and Joint Surg surgery, Jul. 1976, vol. 58-A, No. 5, pp. 636-641.

Sung et al., "Unicameral bone cyst: a retrospective study of three surgical treatments", *Clin Orthop Relat Res*. 2008; 466:2519-26. doi: 10.1007/s11999-008-0407-0.

Toepfer et al., "Bilateral diaphyseal bone cysts of the tibia mimicking shin splints in a young professional athlete?a case report and depiction of a less-invasive surgical technique", BMC Musculoskeletal Disorders, Biomed Central, London, vol. 16, No. 1, Aug. 23, 2015, p. 220; DOI: 10.1186/S12891-015-0668-1.

Urban et al., "Advanced bone regeneration using an injectable CaSO4/CaPO4- TCP composite compared to cancellous bone autograft in a canine model", Paper No. 57, 6th Combined Meeting of the Orthopaedic Research Societies, 2008; 1 page.

Yu et al., "Zoledronate induces apoptosis in cells from fibro-cellular membrane of unicameral bone cyst (UBC)", Journal of Orthopaedic Research, 2005, vol. 23, pp. 1004-1012. DOI: 10.1016/j.orthres.2005.02.012.

Zhang et al., "Treatment of simple bone cysts of the humerus by intramedullary nailing and steroid injection", BMC Musculoskelet Disorder, 2020, 21:70; https://doi.org/10.1186/s12891-020-3054-6.

Zhao et al., "Interventions for treating simple bone cysts in the long bones of children", Cochrane Database of Systematic Reviews, 2017, DOI: 10.1002/14651858.CD010847.pub3.

* cited by examiner

FIGURE 1
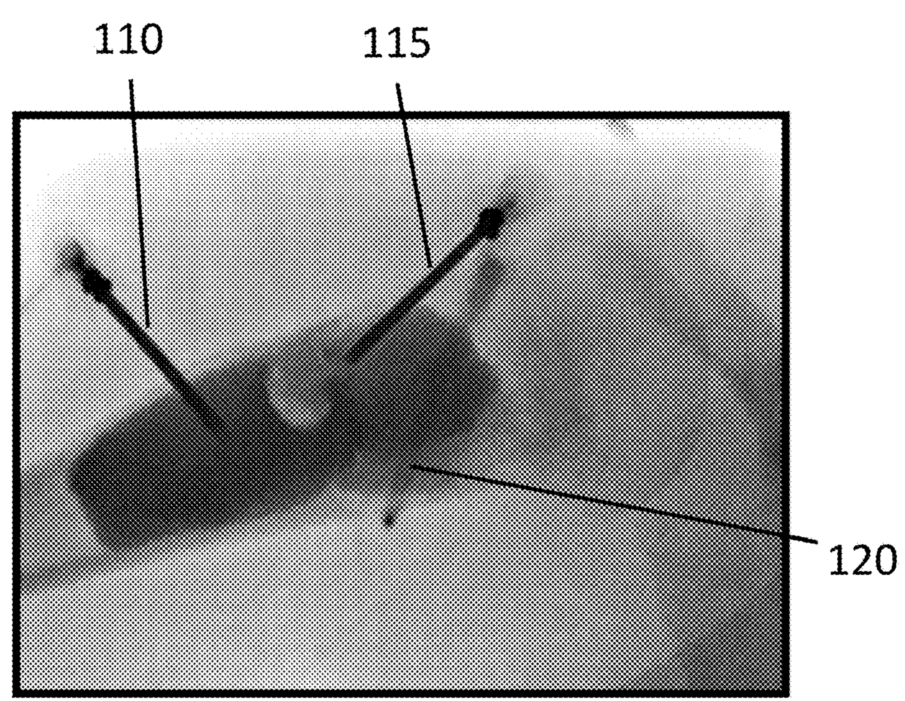
FIG. 1A
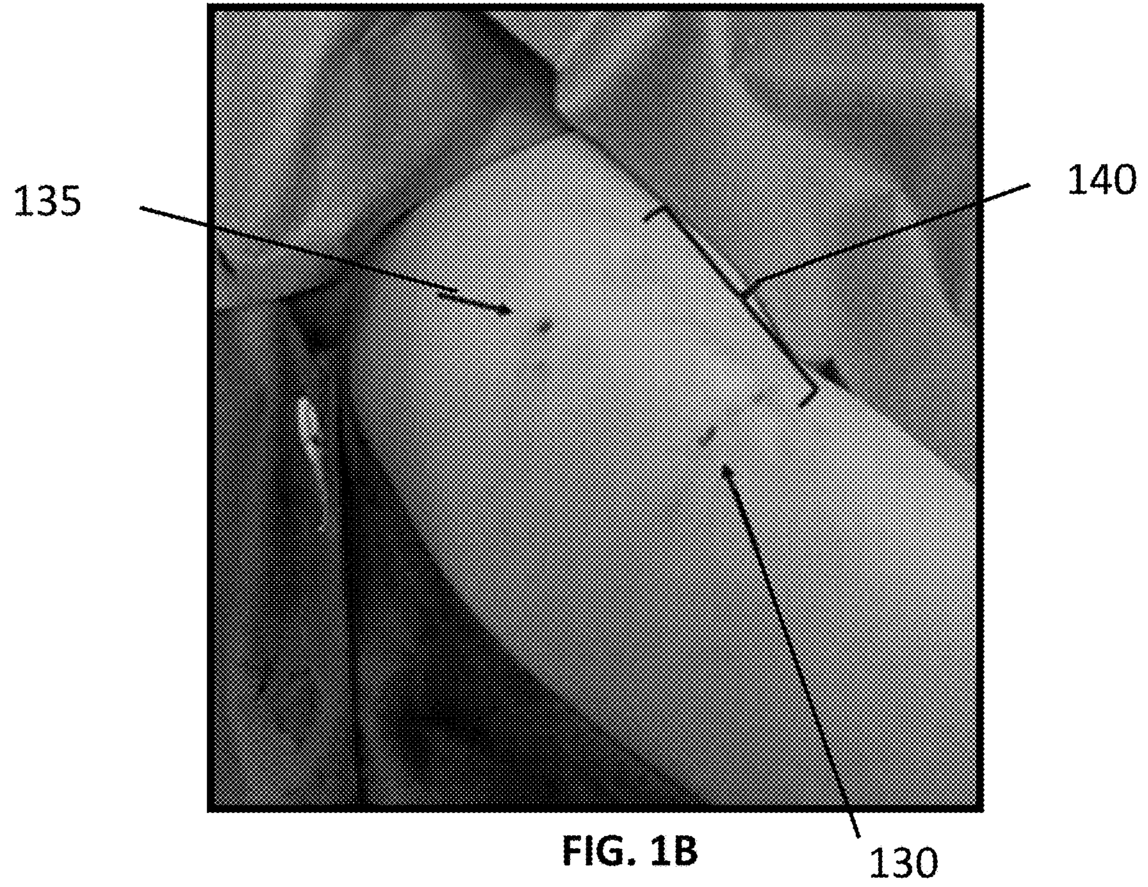
FIG. 1B

FIGURE 2
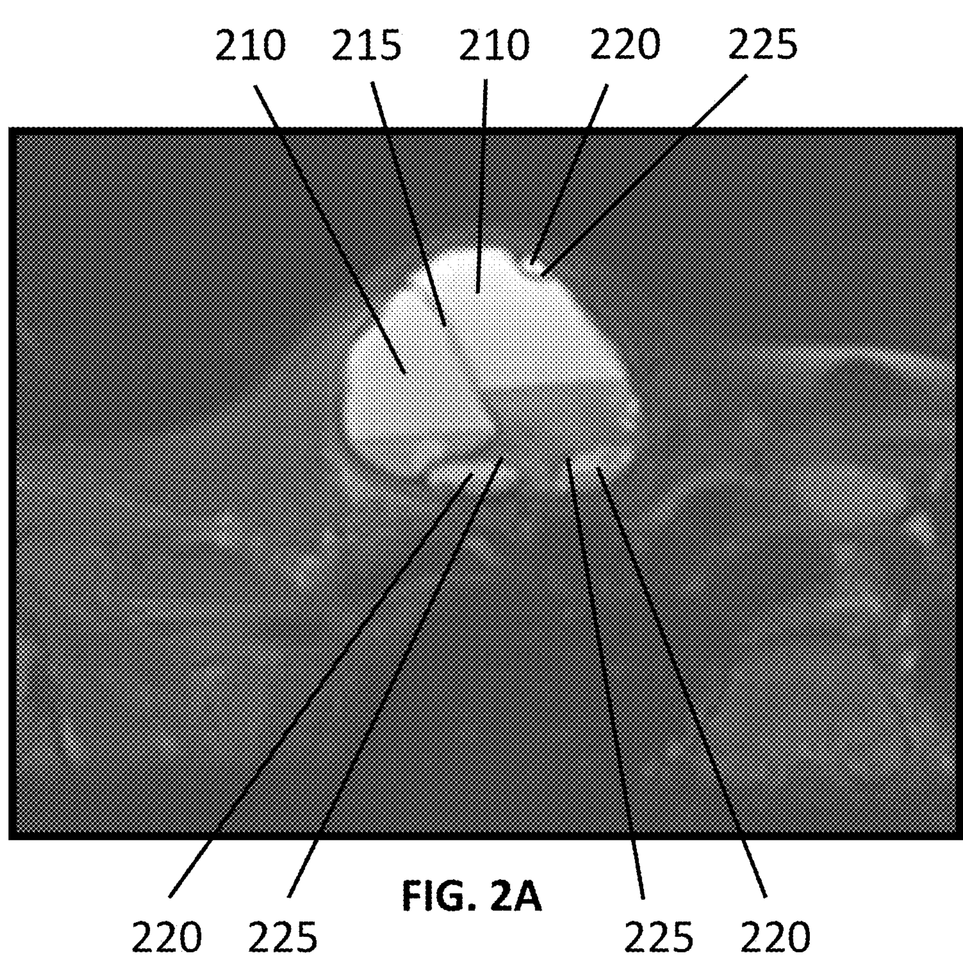
FIG. 2A
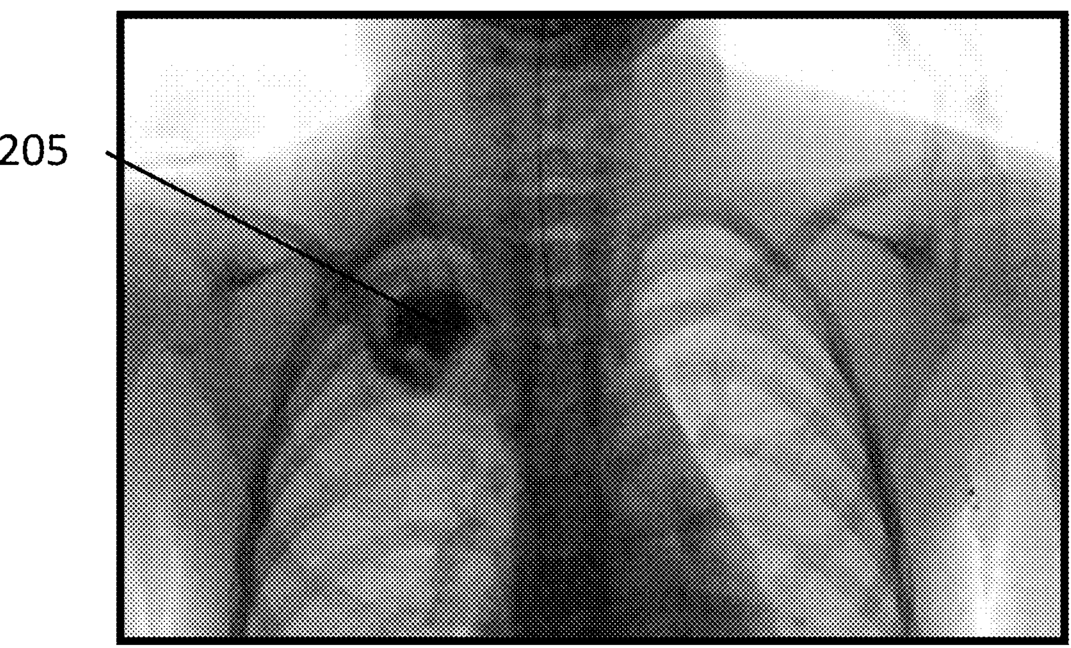
FIG. 2B

FIGURE 5
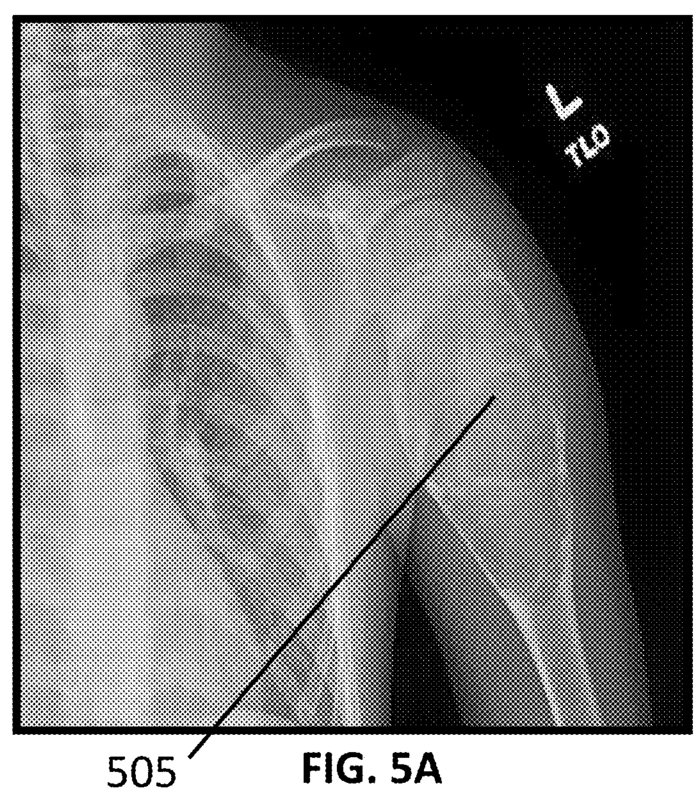
FIG. 5A
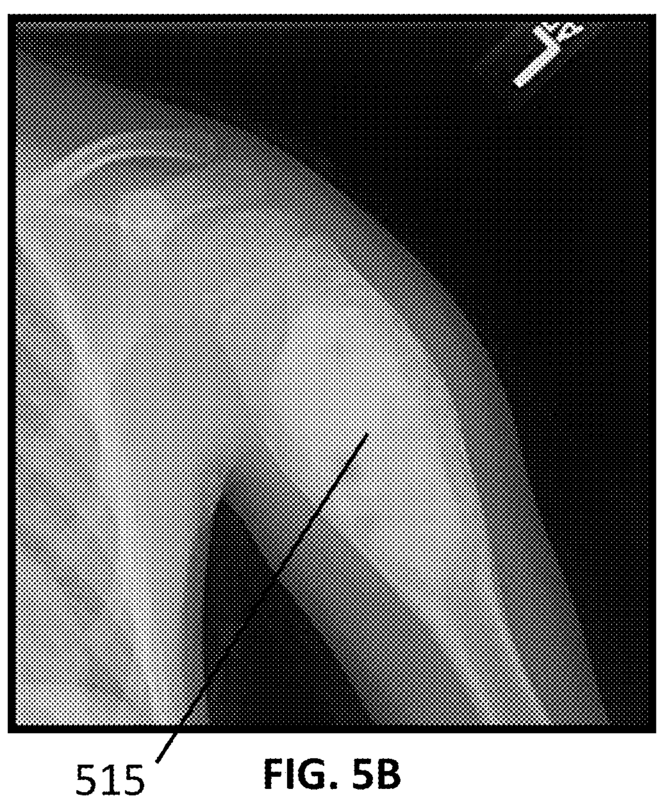
FIG. 5B

SYSTEM AND METHOD FOR TREATMENT OF BONE

CROSS-REFERENCE TO RELATED APPLICATION

This application claims priority to and the benefit of U.S. provisional patent application 63/054,759, filed Jul. 21, 2020, and U.S. patent application Ser. No. 17/379,926, filed Jul. 19, 2021, each of which is incorporated by reference herein in its entirety.

BACKGROUND

Field of the Invention

This invention is directed to systems and methods for treatment of bone with a sclerosing agent and bone graft material, including image-guided and/or minimally invasive treatment of bone lesions such as unicameral and other bone cysts.

Description of the State of the Art

Lesions in the bone, including cystic bone lesions or bone cysts, can cause pain and may predispose a person to fracture and may disrupt bone growth in children.

Simple or unicameral bone cysts (UBCs) are solitary or unilocular bone lesions of unclear etiology. They comprise approximately 3% of primary bone lesions and are most commonly diagnosed in children 5 to 15 years of age. They have a single cavity and tend to arise at long bone metaphyses, most commonly within the humerus and femur. Other bone cysts are septated, and have multiple cavities, for example from two to twenty cavities. Aneurysmal bone cysts (ABCs) are expansile blood-filled bone lesions having numerous channels or cavities. They are less common than UBCs; however, they are more locally aggressive.

Existing treatment approaches for the management of bone cysts are highly variable and recurrence is not uncommon. Treatment options range from watchful waiting to mechanical curettage, in which a curved metal impactor is used to physically disrupt the bone cyst wall, to steroid injection, bone grafting, screw cannulation, metal splints, or a combination of these techniques. There is currently no standardized approach to treatment of bone cysts, and the variable techniques currently performed are associated with relatively high recurrence rates.

Treatment of bone lesions, especially in the pediatric population, often entails multiple and/or a variety of treatments with limited success.

SUMMARY OF THE INVENTION

The invention as described herein provides systems and methods for locating a treatment volume in a bone of the patient, administering a sclerosing agent to the treatment volume, and, after administering the sclerosing agent, administering bone graft material to the treatment volume. In some embodiments, the patient is a pediatric patient.

Embodiments of the invention can further include placing a delivery device into the treatment volume. Administering bone graft material to the treatment volume can include delivering the bone graft material into the treatment volume using the delivery device. Administering a sclerosing agent to the treatment volume can include delivering the sclerosing agent into the treatment volume using the delivery device.

In some embodiments, administering a sclerosing agent to the treatment volume includes using imaging to guide the administration of the sclerosing agent. In some embodiments, placing a delivery device into the treatment volume includes using imaging to guide the placement of the delivery device. In some embodiments, administering bone graft material to the treatment volume includes using imaging to guide the administration of the bone graft material.

In some embodiments, the delivery device comprises a needle. In other embodiments, the delivery device comprises two or more needles. Placing the delivery device into the treatment volume can include placing each of one of more needles into the treatment volume. The size of the needle and/or needles can be determined at least in part by the viscosity of the bone graft material. Less viscous bone graft material can be delivered with smaller (e.g. higher gauge) needles.

In some embodiments, the sclerosing agent comprises one or more of doxycycline, ethanol, sodium tetradecyl sulfate, bleomycin, group A *Streptococcus, Streptococcus pyogenes,* and polidocanol.

Embodiments of the invention can further include placing a venting device into the treatment volume. Administering a sclerosing agent to the treatment volume can include administering a fluid comprising the sclerosing agent to the treatment volume, and administering bone graft material to the treatment volume can cause a portion of the fluid comprising the sclerosing agent to exit the treatment volume through the venting device. The venting device can comprise a first needle. The delivery device can comprise a second needle. The second needle can be larger than the first needle, e.g., the gauge of the second needle can be lower than the gauge of the first needle.

In some embodiments, the treatment volume comprises a single cavity. In some embodiments, the treatment volume comprises a unicameral bone cyst. In some embodiments, the treatment volume comprises a portion of a septated bone cyst. The portion of the septated bone cyst can be the entirety of the septated bone cyst. The septated bone cyst can be an aneurysmal bone cyst.

Embodiments of the invention can further include preparing the treatment volume, for example, before the step of administering the sclerosing agent, for example, by mechanical elimination (e.g. disruption) of tissue within the treatment volume. Preparing the treatment volume can include breaking one or more barriers within the treatment volume. Preparing the treatment volume can include reducing the number of cavities in the treatment volume. In some embodiments, a curette is used to prepare the treatment volume. In some embodiments, an inflatable balloon is used to prepare the treatment volume.

The invention as described herein includes a kit for treatment of a patient, comprising bone graft material, a tube or device for delivery of the bone graft material into a treatment volume of a bone of the patient; and a tube or device for venting a fluid comprising a sclerosing agent from the treatment volume. In some embodiments, the tube for delivery of the bone graft material is also suitable for delivery of the fluid comprising the sclerosing agent. The kit can further include a device for preparation of the treatment volume.

In some embodiments of the kit, the device for preparation of the treatment volume is a curette or an inflatable balloon. In some embodiments of the kit, the bone graft material is in the form of a powder, a putty, a paste, or granules. In some embodiments of the kit, the bone graft comprises a volume of 5 cc, a volume of 10 cc, a volume of 20 cc, or a volume of 40 cc. In some embodiments of the kit, the bone graft material comprises a volume greater than 45 cc. In some embodiments of the kit, the bone graft material comprises a volume greater than 45 cc and less than, for example, 55 cc, 60 cc, 90 cc, 95 cc or 100 cc.

In some embodiments of the kit, the tube for venting is a first needle and the tube for delivery of the bone graft material is a second needle. In some embodiments, the second needle is larger than the first needle, e.g. the gauge of the second needle is lower than the gauge of the first needle. In some embodiments, the second needle has a gauge of 14 or higher (smaller needle) (i.e., the needle is equal in size to or smaller than a 14 gauge needle), and the first needle has a gauge of 14 or higher (smaller needle). In some embodiments, the second needle has a gauge of 14 or lower (larger needle) (i.e. the needle is equal in size to or larger than a 14 gauge needle), and the first needle has a gauge of 14 or higher (smaller needle). In some embodiments, the second needle has a gauge of 18 or higher (smaller needle) and the first needle has a gauge of 14 or higher (smaller needle).

BRIEF DESCRIPTION OF THE DRAWINGS

FIG. 1A shows treatment of a humerus with one needle used for delivery of sclerosant and bone graft material, and a second needle used for venting.

FIG. 1B shows a side-by-side comparison of prior mechanical curettage scar (bracket) compared to stab incisions from the treatment shown in FIG. 1A.

FIG. 2A is an MRI image of a cyst having two dominant cavities and smaller peripheral cavities.

FIG. 2B shows the patient of FIG. 2A after minimally invasive, image-guided treatment with balloon preparation, chemical curettage, and grafting.

FIG. 3A shows a delivery needle, though which a balloon has been inserted into the cyst, and a venting needle. FIG. 3B shows expansion of the balloon within the cyst. FIG. 3C is a 3-dimensional reconstruction image showing the two needles and the volume created by preparation with the balloon. FIG. 3D shows bone graft material administered to the treatment volume, after the administration of sclerosant.

FIG. 4A shows insertion of a delivery device and a venting device into the UBC. FIG. 4B shows bone graft material administered to the treatment volume, after the administration of sclerosant. FIG. 4C shows the treatment volume three months after treatment.

FIGS. 5A to 5B show treatment of a UBC in the humerus of a 9-year-old male, according to one embodiment of the invention. FIG. 5A shows the humerus prior to such treatment. FIG. 5B shows the humerus one month after such treatment.

FIG. 6A shows the humerus before any treatment, evidencing a UBC and fracture. FIG. 6B shows the humerus one year after a prior treatment using mechanical curettage and open application of bone graft material, evidencing recurrence of the cyst.

FIG. 7A shows the femur prior to such treatment. FIG. 7B shows bone graft material administered to a treatment volume, after the administration of sclerosant. FIG. 7C shows the femur approximately 2 months after such treatment.

FIG. 8A shows the femur prior to such treatment. FIG. 8B shows mechanical curettage of the treatment volume. FIG. 8C shows bone graft material administered to a treatment volume, after mechanical curettage and after administration of sclerosant. FIG. 8D shows the femur approximately 2 months after treatment.

DETAILED DESCRIPTION OF THE INVENTION

Figures 3, 3A, 3B, 3C, 3D:
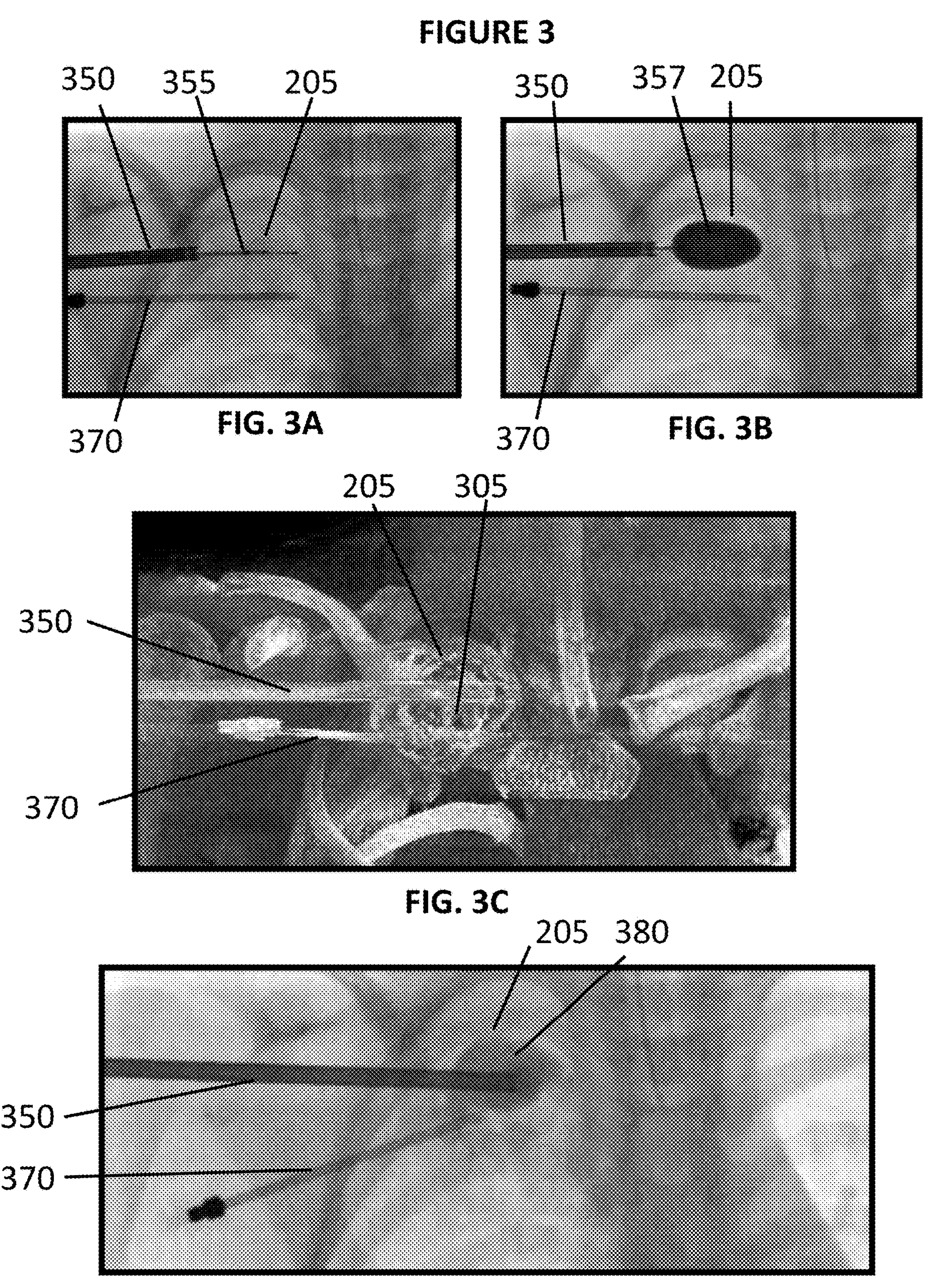
FIGS. 3A to 3D show treatment of the septated cyst shown in FIG. 2A, according to one embodiment of the invention.

This patent describes systems and methods for chemical curettage of bone and administration of bone graft material, including for treatment of unicameral (UBC) and other bone cysts. The systems and methods can use imaging, for example, methods of interventional radiology, to guide the chemical curettage and/or application of graft material. The methods can be minimally invasive and suitable for performance in one or more outpatient procedures. The systems and methods can be minimally invasive and use imaging to guide the chemical curettage and/or application of graft material.

As used herein, "to treat" and "treatment" includes any use of the described methods, and unless otherwise specified, is not limited to treatment of a disease or condition. For the sake of clarity, "to treat" or "treatment" includes use of the methods of the invention for prophylactic or preventive purposes, or without diagnosis of a disease state or condition. As used herein, "treatment volume" refers to a space in a bone, for example, a cavity or pocket or a set of cavities or pockets, that is subjected to the methods described herein. The treatment volume is typically within the bone and can be filled in full or in part with non-bone material, for example, fluid. The treatment volume can encompass bone tissue, for example, the treatment volume may include walls or growths of bone that extend into the treatment volume. In a preferred embodiment, the treatment volume comprises all or a portion of a bone cyst or other bone lesion. In a further preferred embodiment, the treatment volume includes or is the entirety of the bone cyst or other bone lesion.

In a preferred embodiment, this patent describes the administration of a sclerosing agent into the treatment volume, e.g. by injection, followed by the administration of bone graft material into the treatment volume, e.g. by injection. Administration of the sclerosing agent and/or administration of the bone graft material can be accomplished with any device, but preferred devices are those that can effect delivery into the treatment volume without the need for a surgical incision, for example, devices employing a needle or needles as are known for medical use. Such a needle or needles are typically made of thin walled stainless steel and have a hollow center, a beveled end for ease of penetration of tissue, and a hub suitable for fixation to a syringe or other repository of material that is moved through the needle. The sclerosing agent and/or bone graft material can be delivered by a device that does not have a needle, for example, by any device that provides for placement of one end of a tube or tubular element into a patient's bone.

The needle or needles can be of a size that is suitable for subcutaneous injection or larger, for example, the needle or needles can be from about 18-21 gauge (smaller diameter) to about 8-10 gauge (larger diameter). Smaller diameter needles are preferred to minimize impact on and damage to the patient's tissues, but larger needles may be necessary to effect delivery of viscous bone graft material. Less viscous bone material can be delivered with a smaller diameter needle (higher gauge) than more viscous bone material. Currently available synthetic bone graft material can be delivered without complication to relatively large treatment volumes using an 8 to 12 gauge needle, and delivery to small treatment volumes may be feasible with a 14 to 18 gauge needle. A venting needle can be smaller than this, e.g. 18 to 21 gauge.

As used herein, the term "bone graft material" refers to any material conducive to osteogenesis or bone regeneration, including material that can be used to provide an osteoconductive scaffold and/or that supports the growth of osteoblasts and the formation of bone when prepared and administered to bone. Bone graft material can be autograft, allograft, or synthetic. In one preferred embodiment, the bone graft material is synthetic. Preferably, the bone graft material is injectable, for example, after preparation including mixing the bone graft material with a liquid.

Synthetic bone graft materials include, without limitation, hydroxyapatite, tricalcium phosphate, calcium sulfate, and calcium phosphate, and combinations thereof. For example, Collagraft (Zimmer and Collagen Corporation) is a mixture of porous beads composed of 60% hydroxyapatite and 40% tricalcium phosphate ceramic with fibrilar collagen. Other examples of bone graft material products, without limitation, are Norian SRS® (Synthes Inc.), Norian Drillable® (Synthes Inc.), BoneSource® (Stryker Inc.), HydroSet® (Stryker Inc.), Calcibon® (Biomet Inc.), alpha-BSM® (ETEX Corp.), and Callos® (Skeletal Kinetics LLC). Bone graft materials include products that are provided in the form of a power, granules, or putty, a paste, and which may be mixed with liquid to form a compound suitable for use. In one preferred embodiment, the bone graft material is a $CaSO_4$—$CaPO_4$ type of synthetic bone graft material, for example, as provided in GeneX® (Biocomposites) or Pro-Dense® Injectable Regenerative Graft (Wright Medical Technology), for example, a synthetic composite material comprising two calcium phosphate compounds as described in "Pro-Dense® Injectible Regenerative Graft Technical Monograph, by Wright Medical Technology, Inc., 2014 (available at http://www.wrightemedia.com/ProductFiles/Files/PDFs/009555_EN_LR_LE.pdf), incorporated herein by reference.

As used herein, the term "chemical curettage" refers to any administration, e.g. application, exposure, or instillation, of a sclerosing agent to disrupt, destroy, or remove tissue, e.g. in a bone lesion or cyst, including without limitation by injection, irrigation, or the like of a liquid composition comprising the sclerosing agent. Chemical curettage is a form of sclerotherapy. Chemical curettage can be accomplished with any of a variety of chemical agents having sclerosing activity, including without limitation doxycycline, ethanol, sodium tetradecyl sulfate, bleomycin, group A *Streptococcus* (GAS) or *Streptococcus pyogenes*, polidocanol, and similar agents. In one preferred embodiment, the sclerosing agent is the antibiotic doxycycline. Doxycycline has been administered safely to ABCs. The safety and efficacy of doxycycline as a chemical sclerosant is also established in visceral cysts and soft tissue lymphatic malformations. Examples of preparations of sclerosing agents include, but are not limited to including, Acticlate, Adoxa CK, Adoxa Pak, Adoxa TT, Alodox, Avidoxy, Doryx, Docy-100, Mondoxyne NL, Monodox, Morgidox, Oracea, Oraxyl, Periostat Targadox, Vibramycin calcium, Vibramycin Hyclate, Vibramycin monohydrate, Vibra-Tab, Belnoxane, Picibanil (OK-432), Varithena, and Asclera.

In one embodiment, this patent describes an outpatient option for treatment of bone lesions. In one embodiment, this patent describes a minimally invasive, image-guided procedure (MIIP) or technique for treatment of bone.

As used herein, the term "minimally invasive" refers to a surgical technique that limits the damage to the body resulting from a treatment, including methods that limit the size and/or number of any incisions, and which thereby lessen the time required for wound healing or patient recovery, lessen the risk of infection, bleeding, or complication, and/or lessen the pain, discomfort, or impact (e.g. from scarring) on the patient. As used herein, minimally invasive techniques preferably have incisions of less than a few millimeters, most preferably 3 mm or less, and do not require stitches.

As used herein, the term "image-guided" refers to procedures where the surgeon uses preoperative or intraoperative images in order to directly or indirectly guide the placement of a surgical instrument within the patient. For example, a wire, catheter or needle can be placed with the guidance of fluoroscopy, ultrasound (US), computed tomography (CT), or magnetic resonance imaging (MRI). Contrast agents may be introduced to facilitate imaging. Image-guided procedures are commonly performed by interventional radiologists and techniques for image guidance are well-known in the field of interventional radiology.

In a preferred embodiment, the systems and methods are for minimally invasive, image-guided treatment of bone cysts, including but not limited to cystic lesions that occur in the long bones (e.g. the humerus, femur, tibia, clavicles, etc.) and the flat bones (e.g. the pelvis, etc.). In a further preferred embodiment, the systems and methods are for minimally invasive, image-guided treatment of UBCs. In another further preferred embodiment, the systems and methods are for minimally invasive, image-guided treatment of septated cysts, including ABCs.

The systems and methods are particularly useful for treatment of pediatric conditions. The systems and methods can be used for symptomatic and asymptomatic lesions, including lesions that are currently managed conservatively with activity restriction alone.

For example, as shown in FIG. 1A and 1B, two 5 mm stab incisions (incision 130 for insertion of delivery device; incision 135 for insertion of venting device) and two needles (needle 110 serving as a delivery device; needle 115 serving as a venting device) can be used to perform chemical curettage followed by application of bone graft material. Tube 120 suitable for administration of contrast and sclerosis attaches to the needles, allowing syringes to be attached to the tube rather than to the needle, which may help avoid inadvertent dislodging of the needles. The stab incisions heal relatively quickly without stiches and leave minimal scarring 130, 135. In comparison, surgical curettage treatment of the same patient required an incision of 5-6 cm, splaying of the tissue down to the bone, and opening of the bone (so that the cyst could be seen and treated by the surgeon), mechanical curettage of the bone cyst with a surgical tool, followed by application of bone graft material with a spatula into the opening, and closure of the wound with stiches, resulting in a substantial scar 40.

Treatment Volume Preparation

A septated bone cyst has two or more cavities that may be separated, in full or in part, by a wall of bone or fibrous tissue. For example, a clavical aneurysmal bone cyst 205 shown in FIG. 2B, has multiple cavities, as shown in FIG. 2A, including two dominant cavities 210 separated from each other by a wall-like structure 215, and several minor cavities 220, each separated from other cavities by a wall-like structure 225. Treatment of septated cysts may include mechanical elimination of such dividing structures. The walls that create compartments within the cysts can be broken with a surgical device or tool, thereby creating a more open compartment for treatment. For example, a curette or other surgical tool, for example a tool having a small scoop, hook or gouge, can be inserted into a treatment area and used to exert force on the dividing structures sufficient to break them.

In a minimally invasive alternative, an inflatable balloon can be inserted into the treatment area and expanded, thereby exerting force on the dividing structures and breaking them. For example, the KyphX Xpander Inflatable Bone Tamp can be used for such a purpose. As shown in FIGS. 3A-3D, a delivery device 350 and a venting device 370 are inserted into the clavical aneurysmal bone cyst 205. As shown in FIG. 3A, the delivery device 350 is used to insert an unexpanded balloon 355 into the cyst 205. As shown in FIG. 3B, the balloon 355 is then expanded 357, thereby breaking the wall or walls within the cyst and creating a single cavity 305 within the cyst 205, as shown in FIG. 3C. As shown in FIG. 3D, the cyst 205 can then be treated and filled with bone graft 380 delivered through the delivery device 350.

Preparation of septated treatment volumes, e.g. to create fewer and/or large cavities, facilitates access to the entirety of the treatment volume and may improve the quality and/or extent of treatment. For example, such preparation may permit the sclerosing agent to reach more of the cyst wall than would otherwise be possible, and may permit introduction of bone graft material to more of the treatment volume than would otherwise be possible.

Chemical Curettage

The lining of an active bone cyst is known to secrete fluids and enzymes, which may disrupt the underlying bone, for example, causing thinning that disrupts the cortex and/or making a lesion prone to fracture. Mechanical curettage of the cyst membrane lining, typically performed surgically, is known to reduce the risk of recurrence of a bone cyst and/or the need for secondary intervention. It is believed that disrupting the wall lining of an active bone cyst, for example, destroying this lining in full or in part, arrests further fluid secretion into the cyst cavity and thereby arrests cyst progression.

Chemical curettage of a bone cyst is a minimally invasive alternative to mechanical curettage of a cyst wall, for example, the wall of a UBC. Chemical curettage can also be used to treat a cyst volume, for example, the volume of an ABC, or another defined treatment volume, for example, a volume defined as suitable for a single treatment. The system and methods of the invention can be used to treat bone defects resulting from various disease processes.

Chemical curettage of bone is achieved by administration of a sclerosing agent to the treatment volume, for example, by injection into or irrigation of the treatment volume with fluid containing the sclerosing agent. The sclerosing agent is allowed to remain within the treatment volume for a time, and is then displaced, e.g. by administration of bone graft material, or otherwise removed, e.g. by aspiration. One or more such administrations of sclerosing agent can be made, for example, one, two, or thee administrations can be made. The sclerosing agent is allowed to remain in the treatment volume for a period of time, for example, for about 5 to about 30 minutes. In a preferred embodiment, the sclerosing agent is allowed to remain within the bone for eight to fifteen minutes, more preferably for about ten minutes. In a further preferred embodiment, the sclerosing agent is administered twice, in each instanced being allowed to remain within the cyst for eight to fifteen minutes, more preferably for about ten minutes.

Chemical curettage is preferably performed under general anesthesia.

Bone Grafting

Physical or chemical cauterization is believed to impede the underlying disease process of bone cysts. But until bone growth resumes, the bone cortex remains fragile and the treated lesions remain vulnerable to fracture. The introduction of bone graft material into the treatment volume provides increased strength to the compromised bone in the post-procedural period.

In the system and methods of the invention, a minimally invasive mechanism for administration of bone graft material is provided. This mechanism is suitable for administration of bone graft material to treat a UBC without a surgical incision. This mechanism can also be used to treat a cyst volume, for example, the volume of an ABC, or another defined treatment volume, for example, a volume defined as suitable for a single treatment. The system and methods of the invention can be used to treat bone defects resulting from various disease processes.

Administration of bone graft material is achieved by delivering the material into the treatment volume, for example, through an insertable and typically tubular delivery device. In a preferred embodiment, bone graft material is administered by injection with a needle. Preferably, bone graft material that is sufficient to fill the treatment volume is delivered. The bone graft material remains in the bone, providing stability and fostering growth of bone.

Administration of bone graft material is preferably performed under general anesthesia.

The bone graft material can be synthetic. Synthetic bone grafts typically promote faster, denser, and stronger bone regeneration than autologous bone grafts. For example, the bone graft material can be a calcium sulfate-calcium phosphate (CaSO4-CaPO4) material, such as PRO-DENSE (Wright Medical Technology Inc., Arlington, TN). This synthetic bone graft material progresses through a triphasic resorption pattern, with initial resorption of CaSO4, followed by brushite, and finally beta-tricalcium phosphate.

Procedure

The treatment volume must be localized and its volume, dimensions, or general size estimated. This can be approximated prior to a procedure or at the time of the procedure by imaging. A bone cyst or area for treatment can be localized, for example using fluoroscopy or sonographically, and marked on the skin. For example, the upper and lower margins of a UBC can be marked on the skin. In addition, ultrasound mapping of the area of concern can be performed to identify critical structures such as arteries or nerves. Such methods are known to interventional radiologists, but may not be known to orthopedic surgeons.

A delivery device may be placed into the treatment volume. Image-guided techniques can be used to ensure proper placement of the delivery device. Such methods are known in the field of interventional radiology, and include, for example, introduction of a contrast agent into the treatment volume for purposes of imaging. A small incision, e.g. about 5 mm, can be made at the cyst margin as marked on the skin, and the delivery device is then advanced into the cyst percutaneously. The delivery device can be a needle or other tubular tool.

Choice of needle gauge can be determined by the estimated size of the treatment volume, (e.g. the cyst size), viscosity of the bone graft material, and/or the expected amount of synthetic graft to be administered. For example, a 14-gauge needle may be appropriate for many UBCs, but an 11-gauge needle may be preferred for larger cysts to permit delivery of larger volumes of bone graft material. A larger gauge (i.e. smaller diameter) needle may minimize impacts to the patient and may be made possible by lowering the viscosity of the bone graft material or use of less viscous bone graft material.

A venting device should be used for administration of fluids to a closed-compartment target volume, such as a UBC. For example, a second small incision, e.g. about 5 mm, can be made, e.g. at the cyst margin as marked on the skin. The venting device can be a needle, and is advanced into the cyst percutaneously. A venting needle is typically smaller than or the same size as a treatment needle, for example, a 14-gauge or 16-gauge venting needle can be placed for use with an 8-gauge, 11-gauge or 14 gauge treatment needle.

In the absence of a venting device, a closed-compartment target volume may become pressurized, and this may lead to egress of cyst contents, including sclerosants, into systemic drainage via medullary veins, likely decreasing the efficacy of the sclerotherapy. Venous egress of bone graft material due to inadequate venting of the target volume may increase the theoretical risk of devastating venous embolic complications.

The treatment volume can be determined at the time of the procedure via contrast injection into the treatment volume. For example, Omnipaque-180 (GE Healthcare), a water-soluble iodinated contrast, can be diluted with sterile saline and injected via the treatment needle during fluoroscopic visualization, taking care to ensure fluid egress via the venting device. Failure to observe fluid egress via the venting device during injection of the treatment device should alert the physician that one or both of the devices may not be positioned adequately.

Chemical curettage of the treatment volume is achieved by injection of the sclerosing agent through the treatment device. The sclerosing agent can be aspirated through the venting device in a push-pull fashion, irrigating the treatment volume. For example, doxycycline (20 mg/mL), in a volume to match the cyst volume, can be injected through the treatment device, aspirated for one minute, and then allowed to dwell in the treatment volume for another nine minutes. The doxycycline appears yellow prior to initial injection, although is expected to progressively darken during the irrigation process. A second round of sclerosant irrigation can be performed using similar technique and fresh doxycycline solution, in which case the total duration of the sclerotherapy is 20 minutes.

After chemical curettage, bone graft material is delivered to the treatment volume. The volume of bone graft material prepared is based on an estimate of the treatment volume. For example, a volume of bone graft material that is about the same as, or greater than, the treatment volume is prepared. The bone graft material is administered by delivering it into the treatment volume, for example, by injection. The bone graft material is radiopaque and can be delivered during live fluoroscopy. Delivery of the radiopaque synthetic bone graft material should be stopped when either the entire lesion appears opacified with the graft material, e.g. as indicated by exit of the material through the venting device.

After the bone graft material is delivered, the treatment device and venting device can be removed. At the termination of the procedure, the incisions can be covered with sterile dressings. Stitches are typically not necessary and the sterile dressings can be safely removed about 24 to 48 hours later.

While the procedure just described is a minimally invasive procedure, preferably image guided, chemical curettage followed by the introduction of bone graft material could also be performed in an "open" manner, i.e., after making an incision and splaying the tissue down to the bone, and optionally opening the bone. In one such open embodiment, the sclerosing agent can be administered with any of a variety of applicators suitable for irrigation of an opening, e.g. with a syringe. In another open embodiment, the bone graft material can be administered according to current practice, e.g., with a spatula or by injection via large bore needle. In a preferred open embodiment, the bone is not opened, and the sclerosing agent and bone graft material are delivered with one or more needles and/or another tubular delivery device. This avoids unnecessary disruption of the bone structure and may provide for more complete administration of the bone graft material to all portions of the treatment volume.

Evaluation of Treatment

Radiographs can be used to assess the treatment region after chemical curettage and administration of bone graft material. In some embodiments, the bone graft material can be initially hyperdense relative to normal adjacent bone, and can become less dense as it is slowly resorbed. The radiographic evolution of graft material decreasing density should not be confused with cyst recurrence. A recurrence may have cortical bone adjacent to the area of bone graft resorption that is thinned and scalloped.

Factors evaluated on radiographs can include lesion size, amount of new bone formation within the cyst, amount of residual cyst lucency, presence of cortical thickening, and presence of a sclerotic margin. The Modified Neer Classification of Radiographic Healing, shown in Table 1, can be used to classify the degree of healing of a bone cyst.

TABLE 1

| Class | Classification | Description |
|---|---|---|
| 1 | Healed | Cyst filled with new bone, with or without small radiolucent area(s) <1 cm in size, and thickened cortical margins. |
| 2 | Healed with Defects | Radiolucent areas <50% of the diameter of the bone, and the cortical margins had thickened enough to prevent fracture. |
| 3 | Persistent cyst | Radiolucent area >50% of diameter of the bone and no cortical thickening. No increase in the size of the cyst. |
| 4 | Recurrent cyst | Cyst reappearance in a previously obliterated area, or a residual radiolucent area has increased in size. |

The systems and methods described herein provide a high radiographic healing rate and a return to normal activity that is at least comparable to existing surgical techniques. The methods can be less invasive than the existing surgical alternatives, and can thereby lessen the time required for wound healing and patient recovery; lessen the risk of infection, bleeding, and complications; and lessen the pain, discomfort, and general impact on the patient, with better cosmetic outcomes. In addition, the time required to complete a procedure as described herein is generally less than the time required to perform an alternative surgical treatment.

Example 1

Summary. Retrospective evaluation of twelve pediatric patients, ages 5-14 years, undergoing treatment for a UBC, at a single institution. All UBCs were treated in a single, minimally invasive, image guided procedure using percutaneous needle access into the UBC followed by chemical curettage (a form of sclerotherapy) and injection of regenerative synthetic graft. Patients were followed clinically, and with serial radiographs, to evaluate for healing and complications. Mean time to return to full activity was 2.2 months post procedure, with a mean clinical follow-up time of 9.2 months.

Methods. Fifteen patients were initially enrolled in this IRB approved study from August 2018 through May 2020. The diagnosis of UBC was made via radiographs and/or magnetic resonance imaging (MRI).

Combination sclerotherapy and graft injection with $CaSO_4$—$CaPO_4$ was performed in a single setting as an outpatient procedure with an average procedure time of 45 minutes (range 30-60 minutes). Mean volume of doxycycline instilled during cyst sclerotherapy was 52 mL (20 mg/ml and a range 20-100 mL). Mean volume of $CaSO_4$—$CaPO_4$ synthetic graft material administered was 28 mL (range 4-90 mL).

Patients were followed clinically for a minimum of three months post procedure, with radiographs performed at follow-up visits. One patient was excluded as they had imaging consistent with a fractured UBC that had subsequently rehealed into multiple cysts, and 2 other patients were excluded secondary to follow up of less than 3 months.

Assessment of treatment response was evaluated using the Modified Neer Classification of Radiographic Healing, as shown above in Table 1. All radiographs were evaluated by four attending pediatric radiologists. Treatment success in this series was defined as post treatment radiographs exhibiting findings of Modified Neer classes 1 or 2.

Procedure Technique. All procedures were performed under general anesthesia. For each procedure, the cyst was localized under fluoroscopy, and the upper and lower margins of the cyst were marked on the skin. Ultrasound mapping of the area of concern was performed to identify critical structures such as arteries or nerves. However, the cyst itself could often be visualized sonographically due to associated cortical thinning.

Figures 4, 4A, 4B, 4C:
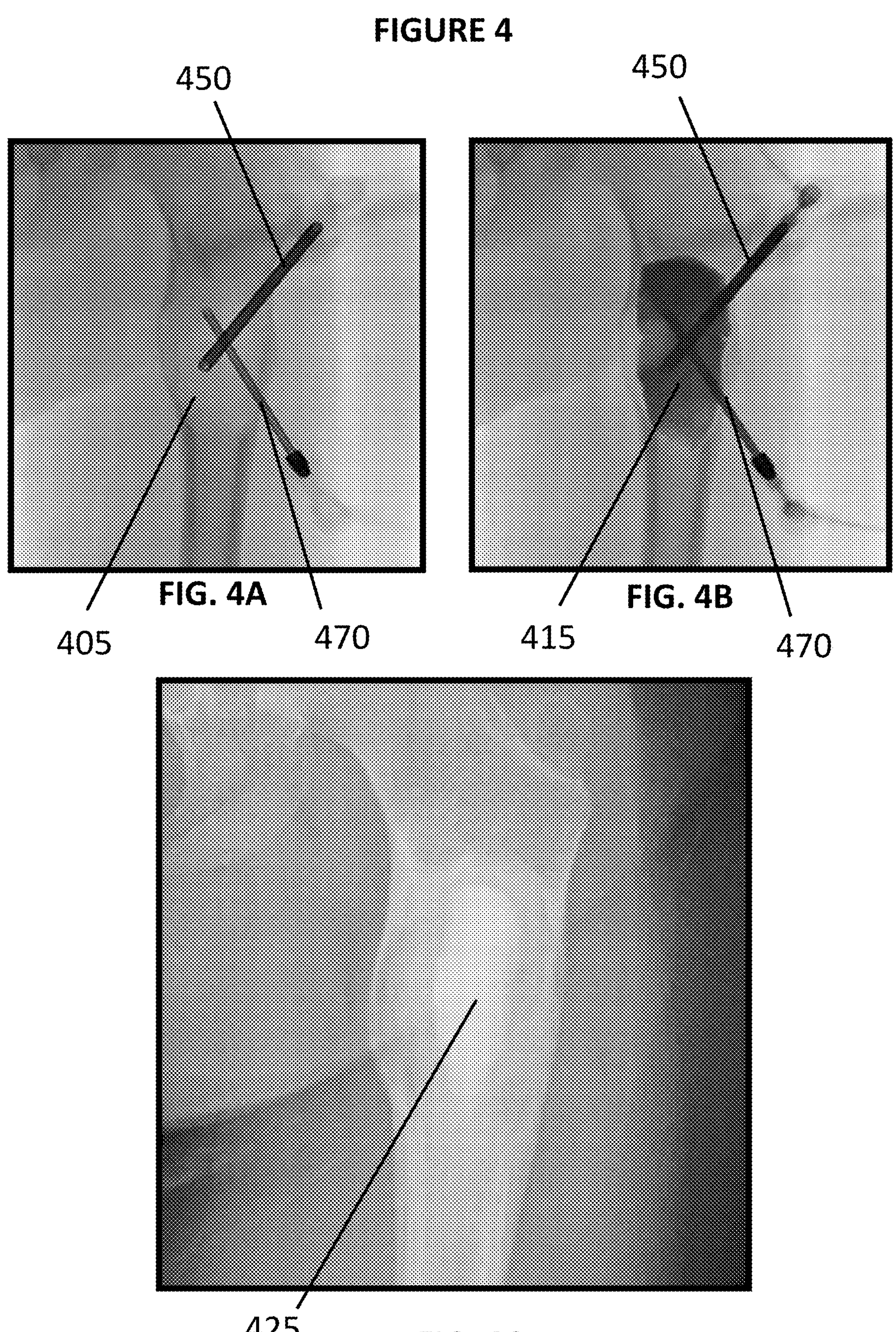
FIGS. 4A to 4C show treatment of a UBC in the femur of a 5-year-old male, according to one embodiment of the invention.

A 5 mm incision was made at each cyst margin as marked on the skin, and an 11-gauge or 14-gauge "treatment" needle was advanced into the cyst percutaneously. Choice of needle gauge was determined by cyst size and the expected amount of synthetic graft to be administered, with 11-gauge needles used in larger cysts. A second 5 mm incision was made along the remaining marked margin of the lesion, and a 14-gauge or 16-gauge "venting" needle was placed. For example, as shown in FIG. 4A, a delivery device 450 comprising an 11-gauge "treatment" needle and a venting device 470 comprising a smaller 16 gauge "venting" needle were positioned within the left proximal femur UBC 405 for a patient who exhibited pain and limp.

Next, Omnipaque-180 (GE Healthcare), a water-soluble iodinated contrast, was diluted with sterile saline in a 1:1 ratio and was injected via the treatment needle during fluoroscopic visualization, taking care to ensure fluid egress via the venting needle. Contrast injection was performed to confirm a cystic nature of the UBC, to ensure adequate diffusion of the injected contrast throughout the cystic cavity, as well as to assess the presence of unexpected significant vascular outflow. Occasionally, an incomplete septation within the cyst was encountered, likely secondary healing change related to a prior pathologic fracture or prior treatment.

Doxycycline (20 mg/mL), in a volume to match the cyst volume, was injected through the treatment needle and aspirated through the venting needle in a push-pull fashion, irrigating the cyst for one minute. The doxycycline was allowed to dwell for another nine minutes. A second round of sclerosant irrigation was then performed using similar technique and fresh doxycycline solution; thus, the total duration of doxycycline sclerotherapy was 20 minutes.

Utilizing the cyst volume determined during initial contrast injection, a similar volume of synthetic bone graft material was prepared and injected through the treatment needle during live fluoroscopy. Injection of the radiopaque synthetic bone graft material was stopped when either the entire lesion appears opacified with the graft material or the material was seen to exit the venting needle. As shown for example in FIG. 4B, this resulted in dense packing of synthetic graft 415 within the cyst 405 after sclerotherapy.

Both needles were removed, and each incision was sterilely dressed. Post procedure activity instructions and limitations varied depending on the patient's cyst size and location; any limitations remained in place until evidence of healing was present on follow-up radiographs. For example, as shown in FIG. 4C, at a 3 month follow up, there was cortical thickening and progressive sclerosis (i.e. stiffening or hardening of the bone) 425 of the left femur UBC 405.

Results. The study population consisted of nine (75%) male patients and three (25%) female patients, with an average age of 9.4 years at the time of treatment (range 5-14, SD 3.0) (Table 2). Seven lesions (58%) were located in the humerus, two (17%) in the tibia, and one in the ilium, the femur, and the navicular bone. Radiographs demonstrated open physes, consistent with skeletal immaturity, in 12 of 12 patients at the time of treatment. Patients either had an MRI, radiographs, or both during their initial clinical evaluation.

Six patients presented with a history of pathologic fracture. For example, as shown in FIG. 5A, one patient presented with left humerus UBC 505 and prior healed pathologic fracture. FIG. 5A is a frontal radiograph that shows a left humerus expansile lucent lesion with cortical thinning, consistent with UBC. FIG. 5B shows increased cortical thickening and dense packing of the synthetic graft 515, consistent with healing, three months post treatment with doxycycline sclerotherapy and synthetic grafting.

Figures 6, 6A, 6B, 6C, 6D:
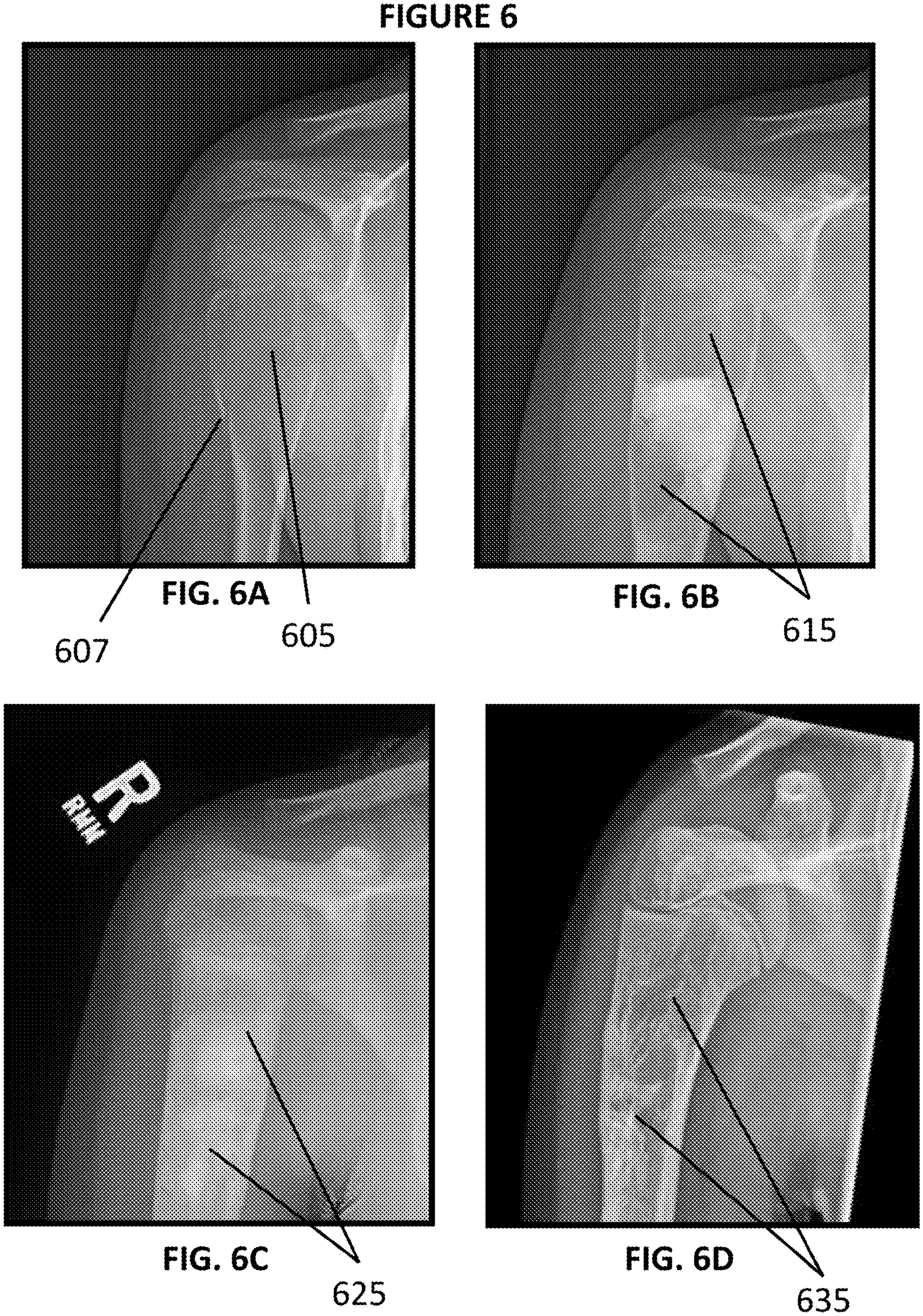
FIGS. 6A to 6B show treatment of a UBC in the humerus of an 8-year-old female, previously treated with traditional methods, according to one embodiment of the invention.
FIG. 6C shows the humerus three months after treatment with chemical curettage and injection of bone graft material.
FIG. 6D shows the humerus one year after the treatment with chemical curettage and injection of bone graft material.

Three patients presented with history of recurrent UBC after prior mechanical curettage and grafting. For example, as shown in FIGS. 6A, one patient presented with right humerus UBC 605 and history of recurrence, including a prior healed pathologic fracture 607, post prior surgical curettage and grafting. FIG. 6A is a frontal radiograph that shows a right humeral UBC with an associated fracture which subsequently underwent surgical curettage and grafting. FIG. 6B is a follow-up radiograph from 1 year later that shows recurrent cysts 615 in the region of the UBC 605. The patient subsequently underwent sclerotherapy and grafting. FIG. 6C shows increased sclerosis (stiffening or hardening) and cortical thickening 625 in the region of the cysts 615 at 3 months post doxycycline sclerotherapy and synthetic grafting. FIG. 6D shows complete graft resorption 635 without evidence of cyst recurrence at 12 months post treatment.

A summary of data for the patients and their treatment is provided in Table 2 below.

Figures 7, 7A, 7B, 7C:
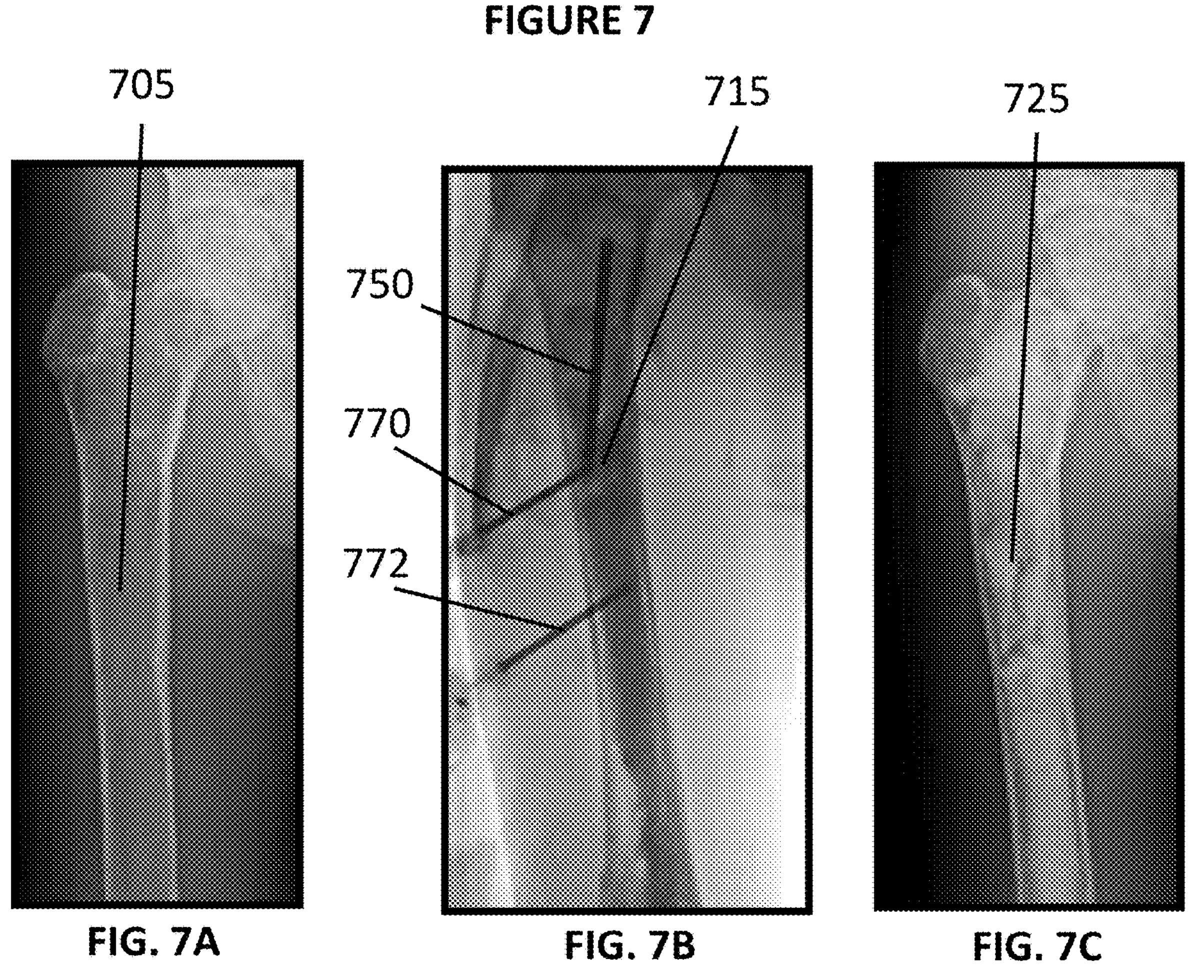
FIGS. 7A to 7C show treatment of a patient according to one embodiment of the invention.

FIG. 7 shows the proximal portion of the patient's femur before 705 (FIG. 7A) and after 725 (FIG. 7C) preparation of the treatment volume, chemical curettage and injection of bone graft material, all performed in a minimally invasive manner with image guidance. FIG. 7B shows the placement of a delivery device 750 having one needle and two venting devices 770, 772, each having a needle, and administration of bone graft material 715 performed as part of this procedure. Bone graft was administered from each needle as the other needles acted as a venting needle and the need for more than one needle was due to the presence of multiple cystic cavities.

TABLE 2

| Patient Number | Age | Sex | Open Physis | Pathologic Fracture Before Treatment | Previous Treatments | Cyst Location | Cyst Size* (cc) | Length of Follow-up (mo) | Radiograph Outcome (Neer) | Return to Activities (mo) |
|---|---|---|---|---|---|---|---|---|---|---|
| 1 | 8 | F | Yes | Yes | Curettage + grafting | R prox humerus | 27 | 18.6 | Healed (1) | 2.8 |
| 2 | 13 | F | Yes | No | No | R prox tibia | 35 | 14.4 | Healed (1) | 3.7 |
| 3 | 7 | M | Yes | Yes | No | L prox humerus | 40 | 8.7 | Healed with defect (2) | 1.0 |
| 4 | 14 | F | Yes | No | No | R prox tibia | 4 | 12.5 | Healed (1) | 0.8 |
| 5 | 5 | M | Yes | Yes | No | L mid humerus | 10 | 10.7 | Healed (1) | 1.9 |
| 6 | 9 | M | Yes | Yes | Curettage + grafting | L prox humerus | 90 | 8.7 | Healed (1) | 2.1 |
| 7 | 8 | M | Yes | Yes | No | L mid humerus | 15 | 4.8 | Healed (1) | 1.3 |
| 8 | 11 | M | Yes | Yes | Curettage + grafting | R mid humerus | 20 | 8.4 | Healed (1) | 1.6 |
| 9 | 10 | M | Yes | No | No | R mid humerus | 14 | 7.0 | Recurrent cyst (4) | 1.2 |
| 10 | 13 | M | Yes | No | No | L iliac wing | 50 | 4.9 | Healed (1) | 1.6 |
| 11 | 5 | M | Yes | No | No | L prox femur | 20 | 4.4 | Healed (1) | 3.1 |
| 12 | 10 | M | Yes | No | No | L navicular | 10 | 7.4 | Healed (1) | 4.8 |

*PRO-DENSE volume used as a surrogate for cyst size

The most recent follow-up radiographs showed healing of the UBC (Modified Neer class 1) in 10 patients (83%) and healing with a small defect (Modified Neer class 2) in one patient (8%). No perioperative complications were observed. In summary, 11 of 12 (91.7%) patients showed healed cysts at their most recent follow-up and there was one case of recurrence noted at 3 months. Patients were pain-free and returned to normal physical activity on average within 2.2 months, and all patients remained asymptomatic at the most recent follow-up. There were no adverse events related to the procedures.

Example 2

A patient was treated with the minimally invasive, image-guided methods described herein.

In this particular case, there was diffuse involvement of the entire right femur resulting in marked morbidity and fracture merely from moving. The decision to treat the whole right femur was made as no appropriate surgical alternative existed. Using techniques similar to those described for treatment of ABCS, seven accesses were performed along the entirety of the right femur, each resulting in placement of a needle, and using a combination of curettes and balloons, the multiple cysts walls were disrupted, the wall linings were sclerosed, and the femur was grafted in its entirety.

Figures 8, 8A, 8B, 8C, 8D:
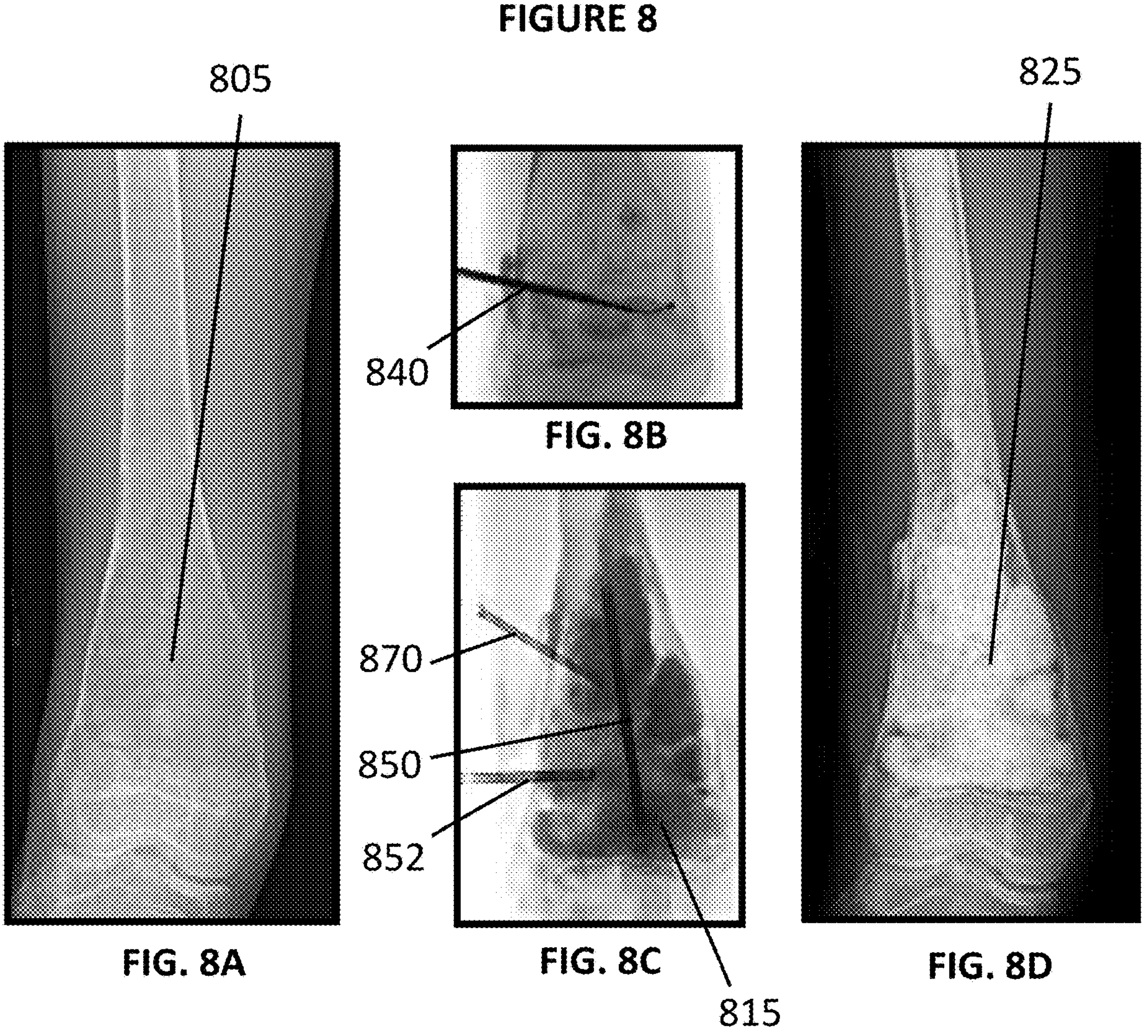
FIGS. 8A to 8D show treatment of the same patient represented in FIGS. 7A to 7C, according to one embodiment of the invention.

FIG. 8 shows the distal portion of the patient's femur before 805 (FIG. 8A) and about two months after 825 (FIG. 8D) preparation of the treatment volume, chemical curettage and injection of bone graft material, all performed in a minimally invasive manner with image guidance. FIG. 8C shows the placement of a venting device 870 and two delivery devices 850, 852 each having a needle, and administration of bone graft material 815 as part of this procedure. FIG. 8B shows mechanical preparation of the treatment volume using a curette 840 to disrupt bone septations, which was done prior to introduction of the sclerosant, as part of this treatment procedure.

Prior to this treatment, a similar procedure was performed on the left humerus of the same patient. Nine months after the procedure, the left humerus showed increased bone cortical thickening and sclerosis (stiffening or hardening) and no fracture.

Example 3

Two patients having ABCs were treated with the methods described here.

One patient presenting with an ABC in the right clavicle, as shown in FIG. 2A, was treated as follows: Image-guided preparation of the treatment volume was completed using a balloon, as shown in FIGS. 3A and 3B; image-guided chemical curettage was performed by percutaneous administration of doxycycline with a needle; and bone graft material was delivered via a delivery needle with placement of a venting needle, as shown in FIG. 3D, filling the treatment volume shown in FIG. 3C, as demonstrated in FIG. 3D.

One patient presenting with an ABC in the right humerus was treated in a similar manner.

Treatment Kit

Embodiments of the invention encompass a kit for performing the methods described herein.

In some embodiments, the kit includes bone graft material. The bone graft material may be in any form, including a powder, granules, or putty, a paste form, that is or can be made suitable for injection into a treatment volume of a bone of the patient. In some embodiments, the kit includes a tube or tubular device suitable for venting the treatment volume of a bone of a patient, and a tube or tubular device suitable for delivery of the bone graft material into the treatment volume. The device suitable for delivery of the bone graft material can be suitable for delivery of a fluid comprising a sclerosing agent into the treatment volume.

In some embodiments, the bone graft material must be mixed with liquid to become suitable for injection into bone. In some embodiments, the device suitable for venting the fluid is a needle and the device suitable for delivery of the bone graft material is a needle. In some embodiments, the needle for deliver is larger than the needle for venting, to accommodate the viscosity of the bone graft material. In some embodiments, the needle for delivery is as small as the venting needle. In some embodiments, the needle for delivery has a gauge of 14 or higher (smaller), e.g. 16 gauge, 18 gauge, or 20 gauge. Smaller needles can be used for delivery of less viscous bone graft material.

In some embodiments, the kit further includes a device for preparation of the treatment volume. The device for preparation of the treatment volume can have one or more expandable components, such as one or more balloons. The device for preparation of the treatment volume can be a surgical tool, e.g. a curette.

Definitions

The phrase "as used herein" encompasses all of the specification, the abstract, the drawings (figures), and the claims.

As used herein, the use of the singular includes the plural and vice versa unless expressly stated to be otherwise, or as obvious from the context that such is not intended. That is, "a," "an" and "the" refer to one or more of whatever the word modifies. For example, "a sample" may refer to one sample, two samples, etc. Likewise, "the sample" may refer to one, two or more samples. By the same token, words such as, without limitation, "samples" would refer to one sample as well as to a plurality of samples unless it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval. As used herein, all numbers which represent physical values or measurements are subject to the standard error in the measurement of the value.

As used herein, any ranges presented are inclusive of the end-points. In addition, throughout this disclosure, various aspects of this invention may be presented in a range format. The description in range format is merely for convenience and brevity and should not be construed as an inflexible limitation on the scope of the invention. Accordingly, the description of a range should be considered to have specifically disclosed all the possible subranges as well as individual numerical values within that range. As an example, a description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Unless expressly indicated, or from the context clearly limited to integers, a description of a range such as from 1 to 6 should be considered to have specifically disclosed subranges 1.5 to 5.5, etc., and individual values such as 3.25, etc. that is non-integer individual values and ranges beginning with, ending with or both beginning with and ending with non-integer value(s). This applies regardless of the breadth of the range.

As used herein, the word "about" may be used to characterize a particular value. When values are expressed as approximations by use of the antecedent "about," it will be understood that the particular value forms another embodiment. As a non-limiting example, if "from about 1to about 4" is disclosed, another embodiment is "from 1 to 4," even if not expressly disclosed. Likewise, if one embodiment disclosed is a temperature of "about 30%," then another embodiment is "30%," even if not expressly disclosed. Similarly, numbers or ranges presented as a specific value or specific range also encompass another embodiment in which the number or the end of the range is preceded by "about." As a non-limiting example, if "an abundance of 30%" is expressly disclosed, then another embodiment is "an abundance of about 30%," even if not expressly disclosed. In a similar manner, if "from 1 to 4" is disclosed, another embodiment is "from about 1 to about 4," even if not expressly disclosed.

As used herein, the use of "preferred," "preferably," or "more preferred," and the like to describe an embodiment refers to preferences as they existed at the time of filing of the patent application.

As used herein, the phrase "and/or" means a combination or an individual member. As a non-limiting example, "X is A, B, and/or C" encompasses the following possibilities: X is A; X is B; X is C; X is any combination of A, B, and C (A and B; A and C; B and C; A, B, and C).

Non-limiting embodiments of the inventions are described in the following paragraphs.

Paragraph (1a): A sclerosing agent for use in a method for treatment of a bone lesion in a patient, the method comprising locating a treatment volume in the bone of the patient, administering the sclerosing agent to the treatment volume, and after administering the sclerosing agent, administering bone graft material to the treatment volume.

Paragraph (1b): Bone graft material for use in a method for treatment of a bone lesion in a patient, the method comprising locating a treatment volume in the bone of the patient, administering a sclerosing agent to the treatment volume, and after administering the sclerosing agent, administering the bone graft material to the treatment volume.

Paragraph (1c): A sclerosing agent and bone graft material for use in a method for treatment of a bone lesion in a patient, the method comprising locating a treatment volume in the bone of the patient, administering the sclerosing agent to the treatment volume, and after administering the sclerosing agent, administering the bone graft material to the treatment volume.

Paragraph (1d): Use of a sclerosing agent for the manufacture of a medicament for treatment of a bone lesion in a patient, wherein the treatment comprises locating a treatment volume in the bone of the patient, administering the sclerosing agent to the treatment volume, and after administering the sclerosing agent, administering bone graft material to the treatment volume.

Paragraph (1e): Use of bone graft for the manufacture of a medicament for treatment of a bone lesion in a patient, wherein the treatment comprises locating a treatment volume in the bone of the patient, administering a sclerosing agent to the treatment volume, and after administering the sclerosing agent, administering the bone graft material to the treatment volume.

Paragraph (1f): Use of a sclerosing agent and bone graft material for the manufacture of a medicament for the treatment of a bone lesion in a patient, wherein the treatment comprises locating a treatment volume in the bone of the patient, administering the sclerosing agent to the treatment volume, and after administering the sclerosing agent, administering the bone graft material to the treatment volume.

Paragraph (2): In some embodiments of the invention, such as but not limited to those described in each of Paragraphs (1a)-(1f), the sclerosing agent is administered in the form of a liquid composition.

Paragraph (3): In some embodiments of the invention, such as but not limited to those described in each of Paragraphs (1a)-(1f) and (2), administering the sclerosing agent disrupts, destroys and/or removes tissue within the treatment volume.

Paragraph (4): In some embodiments of the invention, such as but not limited to those described in each of Paragraphs (1a)-(1f) and (2)-(3), the sclerosing agent comprises or consists of a commercial preparation.

Paragraph (5): In some embodiments of the invention, such as but not limited to those described in each of Paragraphs (1a)-(1f) and (2)-(4), the sclerosing agent comprises doxycyline, for example, Acticlate, Adoxa CK, Adoxa Pak, Adoxa TT, Alodox, Avidoxy, Doryx, Docy-100, Mondoxyne NL, Monodox, Morgidox, Oracea, Oraxyl, Periostat Targadox, Vibramycin calcium, Vibramycin Hyclate, Vibramycin monohydrate, and Vibra-Tab.

Paragraph (6): In some embodiments of the invention, such as but not limited to those described in each of Paragraphs (1a)-(1f) and (2)-(4), the sclerosing agent comprises ethanol or bleomycin (for example, Belnoxane).

Paragraph (7): In some embodiments of the invention, such as but not limited to those described in each of Paragraphs (1a)-(1f) and (2)-(3), the sclerosing agent comprises one or group A *Streptococcus* or *Streptococcus pyogenes,* for example, Picibanil (OK-432).

Paragraph (8): In some embodiments of the invention, such as but not limited to those described in each of Paragraphs (1a)-(1f), and (2)-(3), the sclerosing agent comprises sodium tetradecyl sulfate or polidocanol (for example, Varithena or Asclera).

Paragraph (9): In some embodiments of the invention, such as but not limited to those described in each of Paragraphs (1a)-(1f) and (2)-(10), the bone graft material is synthetic.

Paragraph (10): In some embodiments of the invention, such as but not limited to those described in each of Paragraphs (1a)-(1f) and (2)-(9), the bone graft material is in the form of a powder, a putty, a paste, or granules.

Paragraph (11): In some embodiments of the invention, such as but not limited to those described in each of Paragraphs (1a)-(1f) and (2)-(10), the bone graft material is injectable.

Paragraph (12): In some embodiments of the invention, such as but not limited to those described in each of Paragraphs (1a)-(1f) and (2)-(10), the bone graft material comprises a volume of 5 cc, a volume of 10 cc, a volume of 20 cc, a volume of 40 cc, or a volume greater than 45 cc and less than 55 cc, 60 cc, 90 cc, 95 cc or 100 cc.

Paragraph (13): In some embodiments of the invention, such as but not limited to those described in each of Paragraphs (1a)-(1f) and (2)-(12), the bone graft material comprises one or more of hydroxyapatite, tricalcium phosphate, calcium sulfate, and calcium phosphate (for example, Norian SRS® (Synthes Inc.), Norian Drillable® (Synthes Inc.), BoneSource® (Stryker Inc.), HydroSet® (Stryker Inc.), Calcibon® (Biomet Inc.), alpha-BSM® (ETEX Corp.), and Callos® (Skeletal Kinetics LLC)).

Paragraph (14): In some embodiments of the invention, such as but not limited to those described in Paragraph (13), the bone graft material comprises calcium sulfate and calcium phosphate.

Paragraph (15): In some embodiments of the invention, such as but not limited to those described in each of Paragraphs (13) and (14), the bone graft material is a synthetic composite material comprising at least two calcium phosphate compounds, for example, GeneX® (Biocomposites) or Pro-Dense® Injectable Regenerative Graft (Wright Medical Technology).

Paragraph (16): In some embodiments of the invention, such as but not limited to those described in each of Paragraphs (1a)-(1f) and (2)-(13), the bone graft material is in the form of porous beads and comprises one or more of hydroxyapatite, tricalcium phosphate ceramic and fibrilar collagen.

Paragraph (17): In some embodiments of the invention, such as but not limited to those described in each of Paragraphs (1a)-(1f) and (2)-(16), the administering the sclerosing agent to the treatment volume is performed using a delivery device.

Paragraph (18): In some embodiments of the invention, such as but not limited to those described in Paragraph (17), the delivery device used to administer the sclerosing agent comprises or consists of a needle.

Paragraph (19): In some embodiments of the invention, such as but not limited to those described in each of Paragraphs (17) and (18), the delivery device used to administer the sclerosing agent is placed into the treatment volume using imaging to guide its placement.

Paragraph (20): In some embodiments of the invention, such as but not limited to those described in each of Paragraphs (1a)-(1f) and (2)-(19), the sclerosing agent is administered using a minimally invasive surgical technique.

Paragraph (21): In some embodiments of the invention, such as but not limited to those described in each of Paragraphs (1a)-(1f) and (2)-(20), administering the sclerosing agent to the treatment volume is performed using imaging to guide the administration of the sclerosing agent.

Paragraph (22): In some embodiments of the invention, such as but not limited to those described in each of Paragraphs (1a)-(1f) and (2)-(21), the administering of the bone graft material to the treatment volume is performed using a delivery device.

Paragraph (23): In some embodiments of the invention, such as but not limited to those described in Paragraph (22), the delivery device used to administer the bone graft material comprises or consists of a needle.

Paragraph (24): In some embodiments of the invention, such as but not limited to those described in Paragraph (23) the needle of the delivery device used to administer the bone graft material has a gauge of 8 to 18.

Paragraph (25): In some embodiments of the invention, such as but not limited to those described in Paragraph (23), the needle of the delivery device used to administer the bone graft material has a gauge of 18 to 21.

Paragraph (26): In some embodiments of the invention, such as but not limited to those described in each of Paragraphs (22)-(25), wherein the delivery device used to administer the bone graft material is used to administer the sclerosing agent.

Paragraph (27): In some embodiments of the invention, such as but not limited to those described in each of Paragraphs (22)-(26), the delivery device used to administer the bone graft material is placed into the treatment volume using imaging to guide its placement.

Paragraph (28): In some embodiments of the invention, such as but not limited to those described in each of Paragraphs (1a)-(1f) and (2)-(27), the bone graft material is administered using a minimally invasive surgical technique.

Paragraph (29): In some embodiments of the invention, such as but not limited to those described in each of Paragraphs (1a)-(1f) and (2)-(28), administering the bone graft material to the treatment volume is performed using imaging to guide its administration.

Paragraph (30): In some embodiments of the invention, such as but not limited to those described in each of Paragraphs (1a)-(1f) and (2)-(29), further comprising:

placing a venting device into the treatment volume.

Paragraph (31): In some embodiments of the invention, such as but not limited to those described in Paragraph (30), administering the sclerosing agent to the treatment volume includes administering a liquid composition comprising the sclerosing agent to the treatment volume, and a portion of the fluid comprising the sclerosing agent exits the treatment volume through the venting device upon administering the bone graft material to the treatment volume.

Paragraph (32): In some embodiments of the invention, such as but not limited to those described in each of Paragraphs (30) and (31), the venting device comprises or consists of a needle.

Paragraph (33): In some embodiments of the invention, such as but not limited to those described in Paragraph (32), the needle of the venting device has a gauge of 14 or higher.

Paragraph (34): In some embodiments of the invention, such as but not limited to those described in each of Paragraphs (1a)-(1f), and (2)-(33), the treatment volume comprises all or a portion of the bone lesion.

Paragraph (35): In some embodiments of the invention, such as but not limited to those described in Paragraph (34), the bone lesion is a unicameral bone cyst.

Paragraph (36): In some embodiments of the invention, such as but not limited to those described in Paragraph (34), the bone lesion is a septated bone cyst.

Paragraph (37): In some embodiments of the invention, such as but not limited to those described in Paragraph (34), the bone lesion is an aneurysmal bone cyst.

Paragraph (38): In some embodiments of the invention, such as but not limited to those described in each of Paragraphs (34)-(36), the treatment volume comprises the entirety of the bone lesion.

Paragraph (39): In some embodiments of the invention, such as but not limited to those described in each of Paragraphs (1a)-(1f) and (2)-(38), the method further comprising:

before administering the sclerosing agent, mechanically disrupting tissue within the treatment volume to promote bone growth.

Paragraph (40): In some embodiments of the invention, such as but not limited to those described in each of Paragraphs (1a)-(1f) and (2)-(38), the method further comprising:

before administering the sclerosing agent, mechanically breaking bone tissue within the treatment volume to achieve a less compartmentalized treatment volume.

Paragraph (41): In some embodiments of the invention, such as but not limited to those described in each of Paragraphs (39) and (40), the mechanical disruption is performed with a curette or, alternatively, with an inflatable balloon.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method for treatment of a bone of a patient, comprising:

placing a venting device into a bone treatment volume;

administering a liquid comprising a sclerosing agent to the treatment volume using a minimally invasive surgical technique;

after administering the liquid comprising the sclerosing agent, administering bone graft material to the treatment volume using a minimally invasive surgical technique;

wherein a portion of the liquid composition exits the treatment volume through the venting device upon administering the bone graft material or a further liquid composition to the treatment volume.

2. The method of claim 1, wherein one or both of the liquid comprising the sclerosing agent and the bone graft material is administered using a first delivery device.

3. The method of claim 2, wherein the first delivery device comprises a needle having a gauge of 8 to 18.

4. The method of claim 3, wherein the liquid comprising the sclerosing agent is administered using the first delivery device and the bone graft material is administered using a second delivery device.

5. The method of claim 1, wherein administering bone graft material to the treatment volume is performed using image-guidance.

6. The method of claim 5, wherein the image-guidance is used to place the venting device and a delivery device into the treatment volume.

7. The method of claim 1, wherein the sclerosing agent comprises doxycycline.

8. The method of claim 1, wherein the sclerosing agent comprises one or more of ethanol, bleomycin, group A *Streptococcus, Streptococcus pyogenes*, sodium tetradecyl sulfate, and polidocanol.

9. The method of claim 1, wherein the bone graft material is synthetic.

10. The method of claim 1, wherein the treatment volume comprises a unicameral bone cyst.

11. The method of claim 1, wherein the treatment volume comprises a portion or the entirety of an aneurysmal bone cyst.

12. The method of claim 1, further comprising:

before administering the sclerosing agent, mechanically disrupting tissue within the treatment volume.

13. A kit for treatment of a bone of a patient, comprising:

synthetic bone graft material;

a venting device adapted for exit of a portion of a fluid comprising a sclerosing agent from a treatment volume of a bone of the patient upon administering one or both of a second portion of the fluid and the bone graft material to the treatment volume; and a first delivery device adapted for administering one or both of the sclerosing agent and the bone graft material to the treatment volume in a minimally invasive manner;

wherein the venting device is smaller than or the same size as the first delivery device.

14. The kit of claim 13 further comprising a second delivery device, wherein the first delivery device is adapted for administering the bone graft material to the treatment volume and the second delivery device is adapted for administering the sclerosing agent to the treatment volume.

15. The kit of claim 13, wherein the bone graft material is in the form of a powder, a putty, a paste, or granules.

16. The kit of claim 13, further comprising a curette, an inflatable balloon, or a sclerosing agent.

17. The kit of claim 13, wherein each of the delivery device and the venting device comprises a needle, the needle having a gauge of 8 to 18.

18. The kit of claim 13, wherein each of the delivery device and the venting device comprises a needle, and a gauge of the needle of the venting device is the same as a gauge of the needle of the delivery device.

19. The kit of claim 13, wherein each of the delivery device and the venting device comprises a needle, and a gauge of the needle of the venting device is higher than a gauge of the needle of the delivery device.

20. The kit of claim 13, wherein the venting device is adapted for releasing pressure from the treatment volume.

* * * * *